United States Patent [19]

Ikari et al.

[11] Patent Number: 4,745,129

[45] Date of Patent: May 17, 1988

[54] CHEMICALLY-ACTIVE AQUEOUS SOLUTION AND SOLID SUBSTANCE CONTAINING DIVALENT IRON IONS

[75] Inventors: Yoshikatsu Ikari; Shoichiro Yokoyama, both of Ibaraki; Chiaki Ohama; Ryosuke Fukui, both of Tokyo, all of Japan

[73] Assignee: Technology and Minato Sangyo Co. Ltd., Tokyo, Japan

[21] Appl. No.: 708,076

[22] PCT Filed: Jun. 18, 1983

[86] PCT No.: PCT/JP83/00199

§ 371 Date: Feb. 14, 1985

§ 102(e) Date: Feb. 14, 1985

[87] PCT Pub. No.: WO85/00033

PCT Pub. Date: Jan. 3, 1985

[51] Int. Cl.$^4$ ............ A01N 55/02; A01N 59/16; A01B 79/00; A21D 4/00

[52] U.S. Cl. .................... 514/502; 47/58; 106/15.05; 106/18.11; 106/18.26; 424/147; 426/335; 427/4

[58] Field of Search .......... 424/147; 426/335; 106/15.05, 18.11, 18.26; 47/58; 427/4; 514/502

[56] References Cited

U.S. PATENT DOCUMENTS

| | | | |
|---|---|---|---|
| 1,797,572 | 3/1931 | Fulton et al. | 424/147 |
| 2,381,487 | 8/1945 | Cook | 106/15 |
| 2,411,636 | 11/1946 | Preiswerk | 424/147 |
| 2,822,317 | 2/1958 | Gulesich et al. | 424/147 |
| 3,734,742 | 5/1973 | Morse et al. | 424/147 |
| 3,829,561 | 8/1974 | Heinrich | 424/147 |
| 4,070,488 | 1/1978 | Davis | 424/147 |
| 4,110,508 | 8/1978 | Isgur et al. | 428/240 |
| 4,268,529 | 5/1981 | Davis | 424/147 |
| 4,384,972 | 5/1983 | Nakamura et al. | 252/188.21 |

FOREIGN PATENT DOCUMENTS

| | | |
|---|---|---|
| 45-33737 | 10/1970 | Japan . |
| 52-10884 | 1/1977 | Japan . |
| 54-33287 | 3/1979 | Japan . |
| 54-73140 | 6/1979 | Japan . |
| 55-22317 | 2/1980 | Japan . |
| 57-3416 | 1/1982 | Japan . |
| 2000431 | 1/1979 | United Kingdom . |

OTHER PUBLICATIONS

Chem. Abst. 68 107859(t)(1968)—McCurdy et al.
Chem. Abst. 72:35796c (1970)—Bernath et al.
Chem. Abst. 73:7220n (1970)—Heinrich.
Chem. Abst. 76:131495g (1972)—Morse et al.
Chem. Abst. 95:202,374x(1981)—Florencio.
Chem. Abst. 90:96956z(1979), Maslow slea et al.
Chem. Ab. 55:889i (Lehman 1957).

Primary Examiner—Douglas W. Robinson

[57] ABSTRACT

An aqueous solution or solid substance contains divalent iron ions and L-ascorbic acid. The L-ascorbic acid is present in an amount of 2.0 parts by weight or more per 100 parts by weight of the divalent iron ions. The aqueous solution or solid substance can be used advantageously as deodorants, germicides, foods freshness preserving agents, water treatment agents or the like.

9 Claims, 6 Drawing Sheets

CHEMICALLY-ACTIVE AQUEOUS SOLUTION AND SOLID SUBSTANCE CONTAINING DIVALENT IRON IONS

DESCRIPTION

1. Technical Field

The present invention relates to a novel aqueous solution having various chemical effects such as deodorization, bactericidal action, preservation of freshness of foods, coagulation of pollutants, etc., and more specifically to an aqueous solution containing divalent iron ions in a stabilized state and a solid substance obtained by impregnating with the aqueous solution and then subjecting to a drying treatment.

2. Background Art

Iron (II) compounds such as ferrous sulfate have a wide variety of utility. However, when they are left over in the form of their aqueous solution, ferrous ions are, as well-known in the art, susceptible to ready oxidation by dissolved oxygen or air, whereby they turn to a yellowish brown color and result in the occurrence of a precipitate. It has been known to utilize hydroxylamine, a tin compound or the like as a reducing agent in order to avoid the oxidation of ferrous ions in aqueous solutions. These substances are however highly toxic to the human body, resulting in a limitation in the fields in which aqueous solutions containing divalent iron ions can be applied.

3. Disclosure of the Invention

An object of the present invention is to provide an aqueous solution containing stabilized divalent iron ions. Another object of this invention is to provide new uses for aqueous solutions containing stabilized divalent iron ions.

The present inventors have carried out a variety of investigations on the stabilization of divalent iron ions in aqueous solutions. As a result, it has been found that the addition of a small amount of L-ascorbic acid can unexpectedly stabilize dissolved divalent iron ions while maintaining their effective activities; that the aqueous solution containing the divalent iron ions stabilized by L-ascorbic acid exhibits, owing to a synergistic action of L-ascorbic acid and divalent iron ions, unique chemical activities unavailable from any aqueous solution which does not contain L-ascorbic acid but contains divalent iron ions, thereby providing an aqueous solution useful in a wide variety of fields; and that a solid substance obtained by impregnating a solid material with the aqueous solution and then by subjecting it to a drying treatment and containing L-ascorbic acid and an Iron(II) compound also has unique chemical activities similar to the aqueous solution, leading to the completion of the present invention.

The present invention provides a chemically-active aqueous solution characterized in that said aqueous solution contains divalent iron ions and L-ascorbic acid, the divalent iron ions are present at a concentration of 0.15 wt.% or higher as calculated in terms of metal iron in the aqueous solution, and the L-ascorbic acid is present in a proportion of 2.0 parts by weight or more per 100 parts by weight of the divalent iron ions are expressed in terms of metal iron.

The aqueous solution of present invention may be readily prepared by dissolving an iron(II) compound and L-ascorbic acid in water. As the iron(II) compound, any desired compound may be used so long as it can be dissolved in water to form divalent iron ions. For example, the water-soluble iron(II) salts of inorganic acids such as ferrous sulfate, ferrous chloride, ferrous bromide, ferrous iodide and ferrous nitrate and additionally, water-soluble iron(II) salts of organic acids such as ferrous gallate, ferrous malate and ferrous fumarate may be mentioned. The concentration of divalent iron ions in an aqueous solution is generally 0.15 wt.% or higher or preferably, 0.3 wt.% or higher as calculated in terms of the metal iron in view of the unique chemical activities of the aqueous solution. Its upper limit is the solubility of each iron (II) compound. L-ascorbic acid may be added in an amount or 2.0 parts by weight per 100 parts by weight of divalent iron ions, as expressed in terms of the metal iron in the aqueous solution. Although there is no particulsar limitation on its upper limit, it is desirable from an economical viewpoint to control it to below 30 parts by weight, with 3–10 parts by weight being preferred. If the amount of added L-ascorbic acid should become smaller than 2 parts by weight per 100 parts by weight of divalent iron ions, its effect for stabilizing the divalent iron ions will be reduced. Thus, such small amounts are not preferred.

In an aqueous solution containing divalent iron ions to which L-ascorbid acid has been added in accordance with this invention, the divalent iron ions are stabilized while maintaining their active state. Accordingly, no substantial precipitate will be formed even if the aqueous solution is kept in contact with air for a long period of time. On the other hand, the aqueous solution of the present invention may also be used by impregnating a solid material, which has hygroscopicity, with the aqueous solution. In this case, the solid material impregnated with the aqueous solution is dried to a appropriate degree, thereby causing the solid material to carry the L-ascorbic acid and the iron(II) compound. The combination of L-ascorbic acid and the iron(II) compound, which are both carried on the solid material, also exhibits such unique chemical activities as those seen with the aqueous solution.

Compared with usual aqueous solutions containing divalent iron ions, the aqueous solution of this invention shows various unique chemical activities. As such activities, it is mentioned that it has a significantly high degree of deodorizing effect against malodorous substances containing sulfur or nitrogen, for example, hydrogen sulfide, methyl mercaptan, ammonia, trimethylamine and so on. In an aqueous solution directed to the deodorizing effect, the proportion of L-ascorbic acid may range from 2 to 30 parts by weight, or preferably from 3 to 10 parts by weight per 100 parts by weight of iron(II). In this aqueous deodorant solution, it may be desirable to control the total concentration of L-ascorbic acid and iron(II) compound in the aqueous solution within 0.1–30 wt.% or preferably 1.0–20 wt.%. In order to provide a solid deodorant, this aqueous solution may be impregnated into a solid material such as paper, synthetic paper, fabric, non-woven fabric, porous filler or the like, followed by a drying treatment. In this case, the drying treatment may be omitted in some instances. As such a porous filler, may be mentioned activated carbon, zeolite, bentonite, kaolin, pearlite, sepiolite, diatomaceous earth, silica, alumina or the like. It may have a desired shape, such as powder, granules or the like. The total amount of L-ascorbic acid and Iron(II) compound to be carried on the solid material may be about 0.5–20 parts by weight or so per 100 parts by weight of the solid substance. Paper or non-woven fabric bearing L-ascorbic acid and an iron(II) compound may be discolored when left to stand in air for a prolonged period of time. Such discoloration may however be successfully avoided by additionally incorporating a thiosulfate such as sodium thiosulfate or a dithionite such as sodium dithionite in a suitable amount, for example, one tenth or less of the total amount of the L-ascorbic acid and iron(II) compound.

A deodorant composed of the above-described aqueous solution or solid substance, which is comprised of L-ascorbic acid and an iron(II) compound, may be applied for such purposes in the removal of offensive odor in toilets, garbage pails, refrigerators, drainage openings and the like and the removal of offensive odors in the spaces of room interiors. As to the application of the deodorant, it may be sprayed over each source of offensive odor or may be used as a wash solution to wash each source of offensive odor if the deodorant is in the form of an aqueous solution. If it is in a solid form, it may be applied directly to each source of the offensive odor or, the solid deodorant may be placed in the area containing the offensive odor. The above deodorant may also be used by incorporating it into a part of a sanitary material such as diaper or sanitary napkin.

As the second unique activity of the aqueous solution of the present invention, may be mentioned that it has a bactericidal action and is effective in preserving the freshness of foods. When the aqueous solution of the present invention is applied to perishable foods such as vegetables, fruits, meat, fish and shellfish, and the like, or such processed foods, these foods can be maintained with a high degree of freshness over prolonged periods of time. In this case, the aqueous solution may be applied by coating or spraying it to foods or by dipping the foods in the aqueous solution. Similar to the above-described application as a deodorant, the aqueous solution may be also be impregnated in a solid material such as paper, synthetic paper, non-woven fabric, porous filler or the like and then subjected to a drying treatment in order to convert it into a solid freshness-preserving agent. Regarding application methods of such a solid freshness-preserving agent, in the case of a sheet- or film-like form for example, it may be used to wrap foods. On the other hand, when it is in a powdery or granular form, it may be . . . a suitable drug . . . .

The above-described aqueous solution or solid substance containing L-ascorbic acid and an iron(II) compound can be used as a freshness-preserving agent. Its freshness-preserving effect can be attributed to the strong bactericidal action resulted from the combination of L-ascorbic adid and divalent iron ions. Compositions containing L-ascorbic acid and divalent iron ions may be used as germicides against *Escherichia coli* and other generally known bacteria.

As a further unique activity of the aqueous solution of the present invention, may be mentioned its coagulation-promoting effect for pollutants. When L-ascorbic acid and divalent iron ions are added to water contaminated with pollutants, the pollutants form floc and settle down. An aqueous solution useful as such a water treatment agent may contain L-ascorbic acid and an iron(II) compound at a total concentration of 0.01-20 wt.% or so. Its coagulation effect can be enhanced further by adding to the aqueous solution a small amount of a colloid dispersant such as zeolite, bentonite, silica flour or acid clay. A water treatment agent containing the L-ascorbic acid and iron(II) compounds are particularly superb in its coagulating effect for organic substances such as humic acid, sodium ligninsulfonate, alkali lignin and the like.

As mentioned above, the solution-like or solid-like composition according to the present invention which contains L-ascorbic acid and divalent iron ions has various unique activities. These activities can be attributed to the fact that owing to the action of divalent iron ions in the presence of L-ascorbic acid, molecular oxygen is converted to a super oxide ($O_2^-$) having oxidizing power stronger than the original molecular oxygen upon contact with divalent iron ions. The reactions can be shown by the following equations.

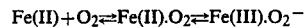

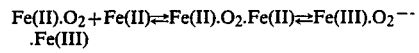

The aqueous solution of the present invention, which contains L-ascorbic acid and divalent iron ions, may be employed, besides for the above-described various unique purposes, for applications which have conventionally been known with respect to aqueous solutions containing divalent iron ions.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

EXAMPLES

The present invention will hereinafter be described in further detail by the following Examples.

EXAMPLE 1

L-Ascorbic acid was added to and dissolved in an aqueous solution of ferrous sulfate (51.7 g Fe/liter), at concentrations up to 5 grams per liter.

A 100 ml portion of each aqueous solution was taken in a 100-ml beaker. The aqueous solution was left to stand in such an open system that a watch glass was merely placed as a lid on the beaker. Changes in the color of the aqueous solution and in the formation of precipitate were observed with the lapse of time.

Test results are shown in the following table.

TABLE 1

| Days left to stand | Changes of Ferrous Sulfate Added with L-Ascorbic Acid with the lapse of Time | | | | | | |
|---|---|---|---|---|---|---|---|
| | Concentration of L-ascorbic acid | | | | | | |
| | 0 mg/l | 500 | 1000 | 2000 | 3000 | 4000 | 5000 |
| 1st day | yellowish green, cloudy | Greenish blue, clear | Greenish blue, clear | Greenish blue, clear | Greenish blue, clear | Greenish blue, clear | Greenish blue, clear |
| 2nd day | ↓ ↓ | ↓ ↓ | ↓ ↓ | ↓ ↓ | ↓ ↓ | ↓ ↓ | ↓ ↓ |

TABLE 1-continued

Changes of Ferrous Sulfate Added with L-Ascorbic Acid with the lapse of Time

| Days left to stand | Concentration of L-ascorbic acid | | | | | | |
|---|---|---|---|---|---|---|---|
| | 0 mg/l | 500 | 1000 | 2000 | 3000 | 4000 | 5000 |
| 3rd day | ↓ | ↓ | ↓ | ↓ | ↓ | ↓ | ↓ |
| 4th day | Precipitation | yellowish green | ↓ | ↓ | ↓ | ↓ | ↓ |
| 5th day | ↓ | ↓ | ↓ | ↓ | ↓ | ↓ | ↓ |
| 6th day | ↓ | ↓ | ↓ | ↓ | ↓ | ↓ | ↓ |
| 7th day | ↓ | ↓ | ↓ | ↓ | ↓ | ↓ | ↓ |
| 8th day | ↓ | ↓ | Yellowish green | ↓ | ↓ | ↓ | ↓ |
| 9th day | ↓ | Cloudy | ↓ | ↓ | ↓ | ↓ | ↓ |
| 10th day | ↓ | ↓ | ↓ | ↓ | ↓ | ↓ | ↓ |
| 11th day | ↓ | ↓ | ↓ | ↓ | ↓ | ↓ | ↓ |
| 12th day | ↓ | Precipitation | ↓ | Yellowish green | ↓ | ↓ | ↓ |
| 13th day | ↓ | ↓ | ↓ | ↓ | ↓ | ↓ | ↓ |
| 14th day | ↓ | ↓ | ↓ | ↓ | ↓ | ↓ | ↓ |
| 15th day | ↓ | ↓ | ↓ | ↓ | ↓ | ↓ | ↓ |
| 16th day | ↓ | ↓ | ↓ | ↓ | ↓ | ↓ | ↓ |
| 17th day | ↓ | ↓ | Cloudy | ↓ | ↓ | ↓ | ↓ |
| 18th day | ↓ | ↓ | ↓ | ↓ | Yellowish green | Yellowish green | Yellowish green |
| 19th day | ↓ | ↓ | Precipitation | ↓ | ↓ | ↓ | ↓ |
| 20th day and up | ↓ | ↓ | ↓ | Blackish yellow | Blackish yellow | Blackish yellow | Blackish yellow |

Figure 1:
FIG. 1 to FIG. 4 are graphs showing respectively test results of Example 1.
Figure 2:
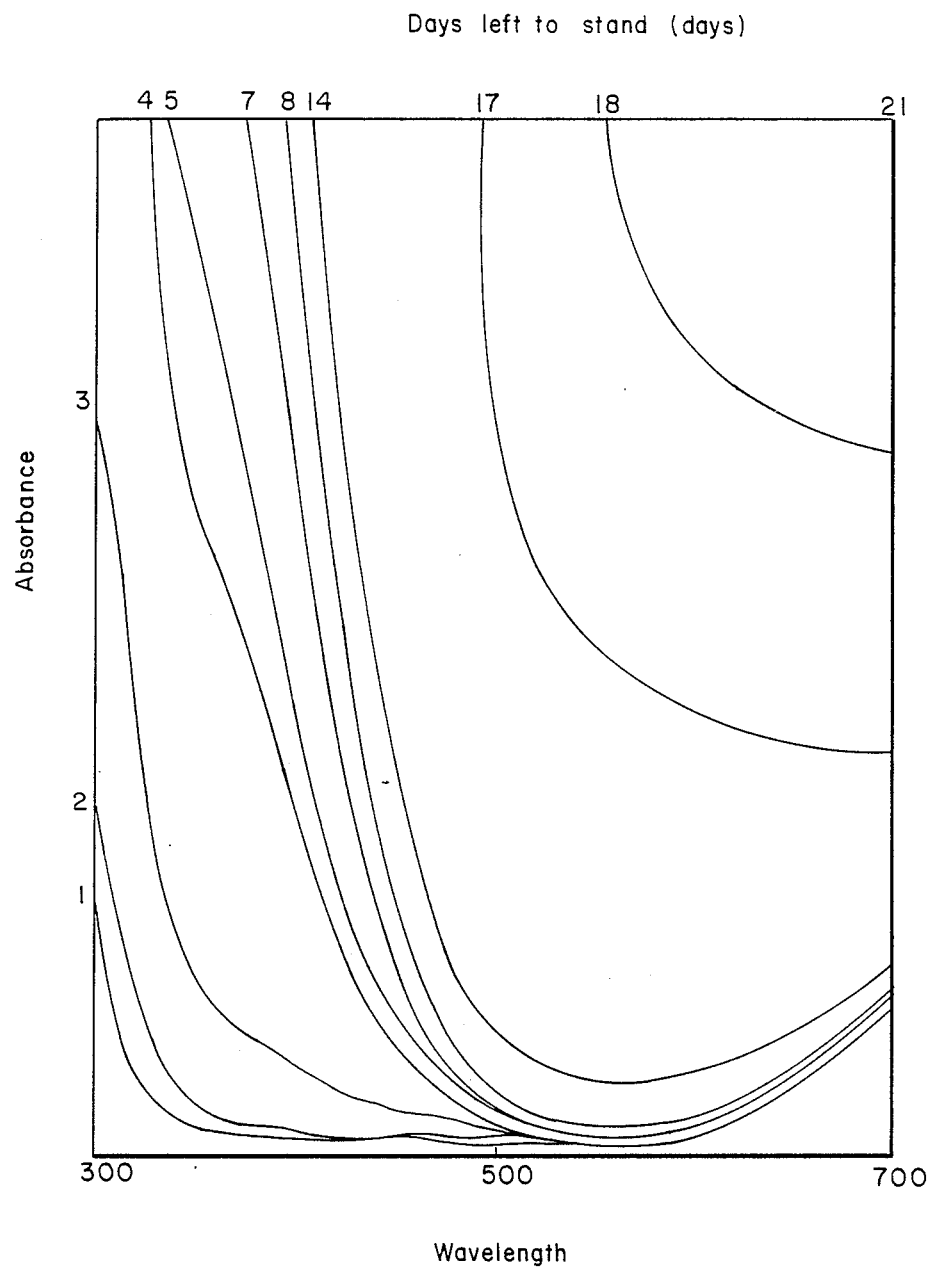
Figure 3:
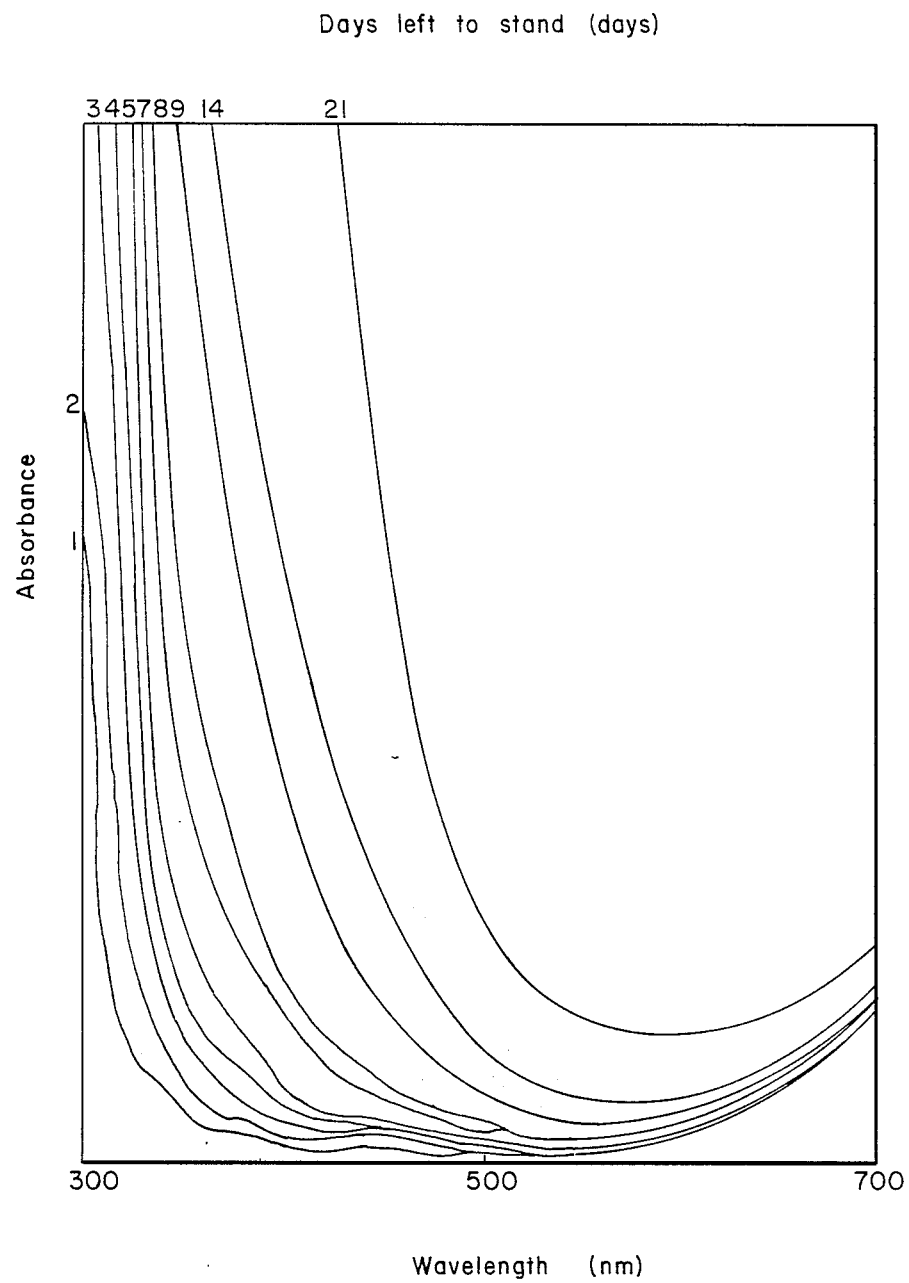
Figure 4:
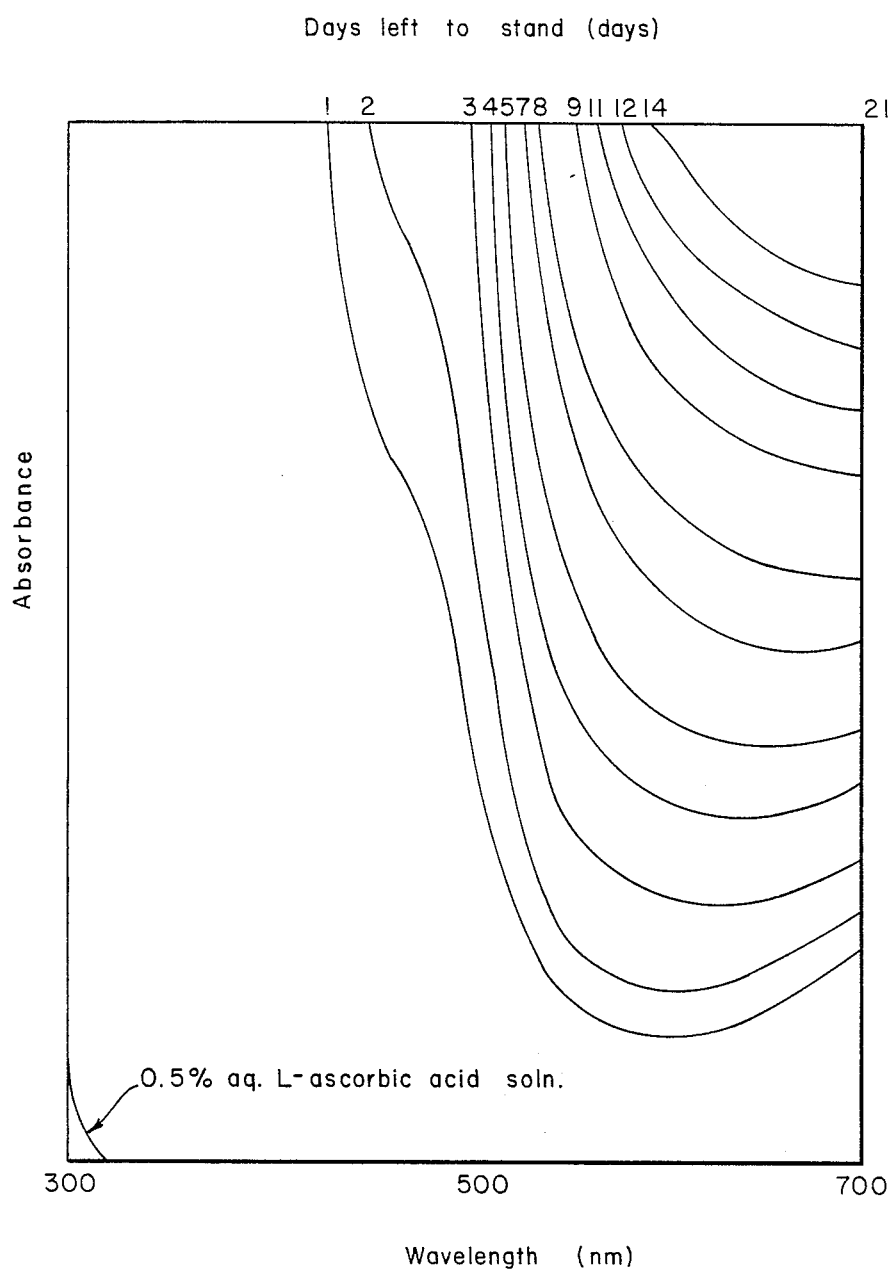

The chromaticity was measured by UV-300 on each of the above-described aqueous ferrous sulfate solutions which were each treated with L-ascorbic acid. The results are shown in FIG. 1 to FIG. 4, where the absorption spectrum is shown for every passing day. The added amounts of L-ascorbic acid were respectively 0.5 g/liter, 1 g/liter and 2 g/liter respectively in FIG. 1 to FIG. 3. FIG. 4 corresponds to a control free of added L-ascorbic acid, which is shown for the sake of comparison. From the results of FIG. 1, it is appreciated that with the addition of 0.5 g, the aqueous ferrous sulfate solution remained substantially stable up to the 7th day but developed changes with the passage of time after the 8th day. As also apparent from FIGS. 2 and 3, the corresponding aqueous ferrous sulfate solutions were increasingly stabilized to significants as L-ascorbic acid was added more and more and in the case of FIG. 3 (added amount: 2 g), the aqueous ferrous sulfate solution did not show any substantial changes until 21th day.

On the other hand, in the case of FIG. 4 which corresponds to the aqueous solution without L-ascorbic acid, no stabilization is observed on the absorption spectrum. Thus, it is clearly demonstrated that the aqueous solution underwent changes with the lapse of time.

EXAMPLE 2

One hundred milliliters of an aqueous solution containing 15% of ferrous sulfate, 2.5% of magnesium oxide, 0.4% of acid clay and 0.4% of natural zeolite (all by wt.%) were diluted to 1 liter under hydrochloric acid condition. To portions of the thus-diluted solution, L-ascorbic acid was added respectively at varied levels up to 20 g to prepare flocculant containing L-ascorbic acid.

On the other hand, a humic acid solution of COD 50 mg/liter was also prepared as sample solution to be treated.

In a beaker, 490 ml of the above sample solution was placed. After stirring it at 150 rpm, 10 ml of one of the above coagulants was added, followed by a pH adjustment with hydrochloric acid or a sodium hydroxide solution to 7.0.

Figure 5:
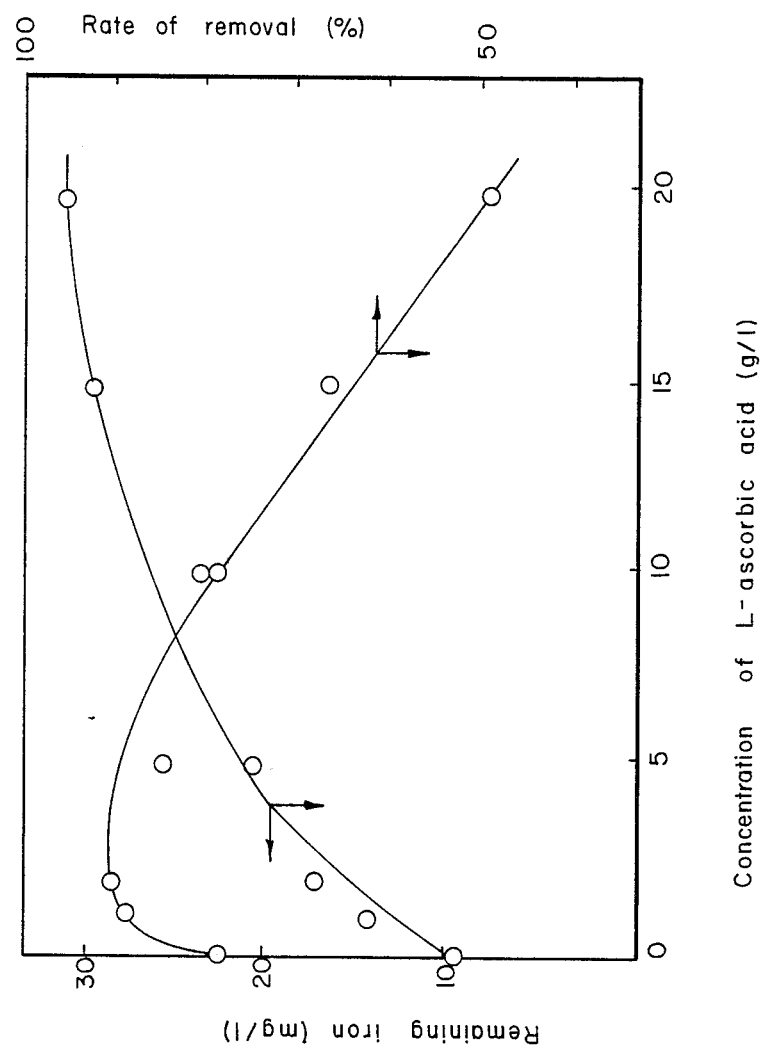
FIG. 5 is a graph showing test results of Example 2.

After the pH adjustment, the resultant solution was stirred at 150 rpm for 5-10 minutes and then at 60 rpm for 15 minutes. Upon completion of the stirring, the solution was centrifuged and then filtered through a 5C filter paper to provide a sample. Percent of organic substances removed and remaining iron were measured on the sample. Results are shown in FIG. 5. From these results, it is appreciated that by addition of L-ascorbic acid up to 10 g/liter, the percent of humic acid removed went up considerably. Moreover, the remaining iron was measured by oxidizing the sample with air under neutral to mild alkaline (pH 7-8) conditions in accordance with a method known per se in the art to remove iron.

EXAMPLE 3

(A) Preparation of iron L-ascorbate:

After dissolving 25.7 g of ferrous sulfate hyptahydrate (molecular weight: 278.03) with deionized water to 100 ml, 0.5 g of L-ascorbic acid was added and dissolved to prepare an aqueous bactericidal solution of iron L-ascorbate.

(B) Bactericidal test:

(1) Water to be treated:

Water was collected on July 27, 1982 near Morinosato, Lake Ushiku, Ibaraki for use in the present test.

(2) Procedure of bactericidal test:

A 100 ml portion of the sample water was placed in a 100-ml beaker which had in advance been simply sterilized in dry and hot air. The sample water was agitated vigorously, to which 1 ml of one of the solutions prepared by diluting the above aqueous solution of iron L-ascorbate to 1-100 times. Samples were collected respectively upon elapsed time of 5 minutes, 10 minutes, 15 minutes and 30 minutes. In a manner which is described below, culturing tests were carried out using deoxychlolate culture medium to determine the numbers of colonies of *Escherichia coli*.

(3) Procedure of culturing tests:

When a sample was expected to contain 300 colonies or more of *Escherichia coli* per milliliter, 9 ml or 99 ml of a phosphate-buffered aqueous diluent was added to 1 ml of the sample to dilute it. The sample was diluted further when needed, thereby preparing a diluted sample capable of providing 30-300 colonies of *Escherichia coli* per milliliter after culturing.

Thereafter, 1 ml of the sample was placed in a sterilized Petri dish, to which about 10 ml of deoxycholate culture medium which had been kept at about 48° C. subsequent to its heating and dissolution was added. Then, the Petri dish was shaken to mix the culture medium thoroughly with the sample. When the resultant mixture was spread all over the sterilized Petri dish, the Petri dish was left over horizontally so as to allow the mixture to coagulate. After the coagulation of the mixture, 5-10 ml of deoxycholate culture medium was added further to over the entirety of the coagulated surface, followed by its coagulation as an ovelaid layer.

After the coagulation, the sterilized Petri dish was turned upside down and placed in an incubator, in which the sample was cultured at 36±1° C. for 18-20 hours. Red to Crimson colonies which had occurred on the culture medium and had substantially the same shape were counted. Their average number was then determined to show the number of colonies per ml of the sample. In the case of a diluted sample, a sterilized Petri dish resulted in the occurrence of 30-300 colonies was taken out and the number of colonies per ml of the sample was determined.

Figure 6:
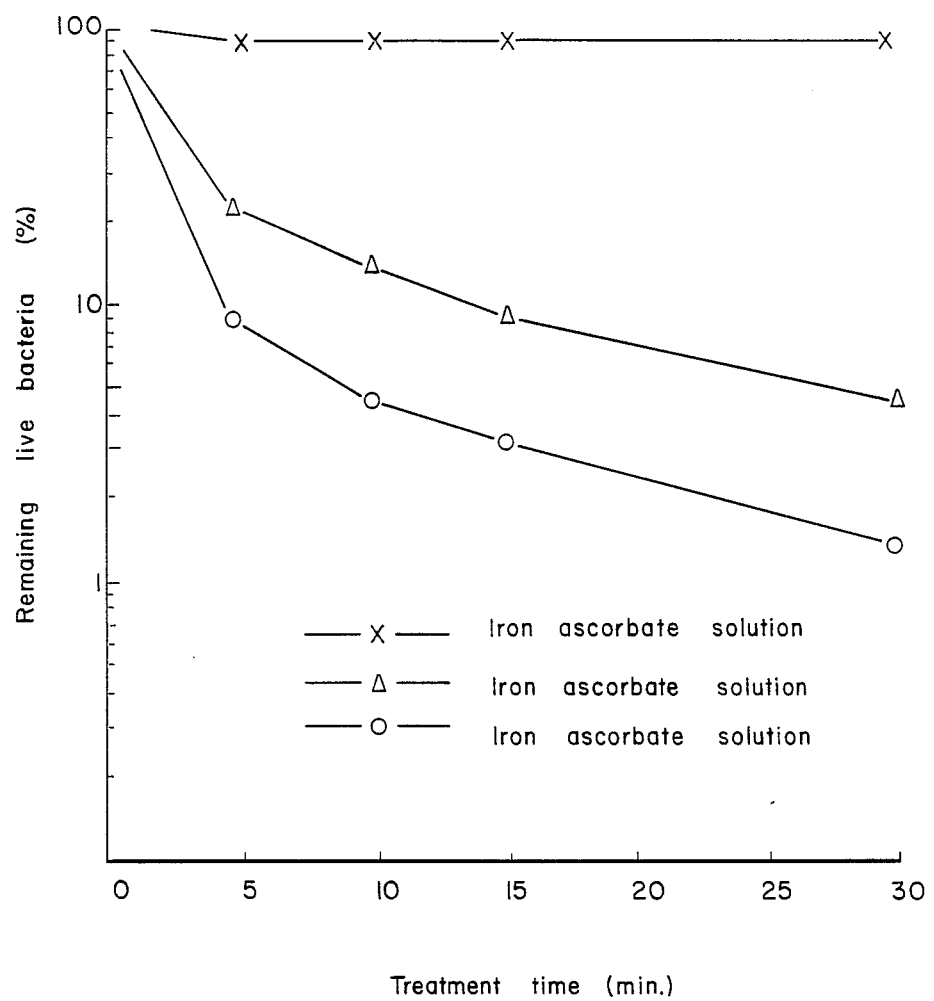
FIG. 6 is a graph showing test results of Example 3.

(C) Results of bactericidal tests:

The percentage of remaining live bacteria was obtained by determining the proportion (%) of the number of colonies of *Escherichia coli* in each steritized sample to the number of colonies of *Escherichia coli* in the untreated water. The relationship between the time (min.) of bactericidal treatment by aqueous iron L-ascorbate solutions of various concentrations and percent remaining live bacteria is shown in FIG. 6.

From the results shown in the figure, the bactericidal efect of ascorbic acid is not observed to any significant degree at the iron ascorbate concentration of 0.01% or so even when a contact time period of 30 minutes was given. However, remarkable effects were observed with concentrations of 0.1% and up. Its sterilizing activity has been found to increase further when added at 1%. These effects cannot be expected from any iron(II) solution. Furthermore, no bactericidal effects can be exhibited with ascorbic acid concentrations of such low levels. As demonstrated above, an addition of iron ascorbate in such a small amount of 0.1% or so can colonies of *Escherichia coli* without secondary influence. It is thus understood that the above effects, which are not extremely strong, can be used widely for many purposes.

EXAMPLE 4

(A) Preparation of an antiseptic preservative material impregnated with iron L-ascorbate:

Using water, 27.5 g of ferrous sulfate heptahydrate (molecular weight: 278.03) was dissolved to 100 ml. Then, 0.5 g of L-ascorbic acid was added and dissolved to prepare an undiluted aqueous iron L-ascorbate solution.

Thereafter, the undiluted solution was diluted to 5 times. The thus-diluted solution was then sprayed by a sprayer on the entire front and back surfaces of each of kraft paper bags (33.2 cm long and 24 cm wide). After spraying the solution to 15 wt.%, the bags were dried at room temperature.

(B) Freshness-maintaining tests:

Untreated kraft paper bags were provided for the sake of comparison, along with the above-described kraft paper bags subjected to impregnation with iron L-ascorbate. Newly-bought commercial boiled fish paste (product of Marumata Kamaboko Seizo Yugen Kaisha; 220 g), frozen (and thawed) prawns (85 g) and seedless grapes or Kyoho grapes (120 g) were respectively packed and sealed in both of the bags. At room temperature (20° C.), changes in the freshness of each foods along the passage of time and development of rotting (mold, slime, putrid smell) were compared and observed. Results are shown in the following table.

From the results in the following table, it is envisaged that according to this invention, boiled fish paste, seedless grapes and Kyoho grapes can be preserved for a longer period by about 7 more days on average than the comparative examples. Even in the case of frozen prawns, the present invention allows it to last more as many as about 5 more days on average compared with the comparative examples.

TABLE 2

| Foods | | 1st day | 2nd day | 3rd day | 4th day | 5th day | 6th day |
|---|---|---|---|---|---|---|---|
| Boiled fish paste | This invention | 1 No change | No change | No change | No change | No change | No change |
| | Comparative example | 2 No change | No change | With mold occurred on the base plate | A little yellow mold occurred | yellow mold spread little by little | Black spot occurred on the base plate |
| Frozen (and thawed) prawns | This invention | 1 No change | No change | No change | No change | No change | Slime occurred on the surface |
| | Comparative example | 2 No change | A little putrid smell | Slime occurred on the surface | Putrid smell became stronger | Both putrid smell and slime spread | Putrid smell and slime both aggravated, shape changed |
| Seedless grapes | This invention | 1 No change | No change | No change | No change | No change | No change |
| | Comparative example | 2 No change | No change | Stalks browned | Brown color spread over stalks and | Stalks browned severely | Brown parts of stalk turned gradually to |

TABLE 2-continued

| | | | | | | | | |
|---|---|---|---|---|---|---|---|---|
| Kyoho grapes | This invention | 1 | No change | No change | No change | grapes lost luster<br>No change | No change | black<br>No change |
| | Comparative example | 2 | No change | No change | Grape surfaces changed in color | Stalks became black | Grape shape soft | changed |

| | Foods | | 7th day | 8th day | 8th day | 9th day | 10th day |
|---|---|---|---|---|---|---|---|
| | Boiled fish paste | This invention | No change | No change | No change | No change | White mold occurred |
| | | Comparative example | Green mold occurred on the base plate | Mold of various colors spread | Mold of various colors spread | Mold of various colors spread | Mold of various colors spread |
| | Frozen (and thawed) prawns | This invention | No putrid smell | Slight putrid smell occurred | Slight putrid smell occurred | Slime occurred on the surface and putrid smell somewhat aggravated | Surface slime and putrid smell aggravated further |
| | | Comparative example | Putrid smell and slime both aggravated, shape changed | Putrid smell and slime both aggravated, shape changed | Putrid smell and slime both aggravated, shape changed | Putrid smell & slime both aggravated, shape changed | Putrid smell and slime both aggravated, shape changed |
| | Seedless grapes | This invention | No change | No change | No change | No change | Stalk ends turned to brown |
| | | Comparative example | Green parts of stalk shrunk down little by little | Grape shapes changed | Grape shapes changed | Grape shapes changed and grapes rotted | Rotting of grapes spread |
| | Kyoho grapes | This invention | No change | No change | No change | No change | Some changes occurred on the skins of grapes |
| | | Comparative example | White mold occurred on the skins of grapes | Mold spread on the skins of grapes | Mold spread on the skins of grapes | White mold gradually tinged | Holes formed in grapes |

EXAMPLE 5

After dissolving 27.5 g of ferrous sulfate heptahydrate (molecular weight: 278.03) in water to form 100 ml of a solution, 0.5 g of L-ascorbic acid was added to and dissolved in the solution to prepare an undiluted aqueous solution of iron L-ascorbate.

Thereafter, the undiluted aqueous solution of iron L-ascorbate was diluted to a 10 times of volume with water to prepare a liquid deodorant.

Then, 10 g portions of fowl droppings were placed respectively in two scrubbing bottles (each 100 ml in volume). Fifty milliliters of purified water were added to one of the scrubbing bottles and 50 ml of the liquid deodorant to the other scrubbing bottle. The scrubbing bottles were allowed to stand for 24 hours in an incubator of 37° C. After that, gases produced respectively in the scrubbing bottles were each purged out with 20 liters of pure air. They were collected respectively in bags and the amounts of hydrogen sulfide, methyl mercaptan and ammonia in each of the gases (deodorized gas and untreated gas) were measured. Measurement results are shown in Table 3.

EXAMPLE 6

Granular activated carbon (produced by a method known per se in the art, namely, extrusion-forming a mixture which contained 20 parts by weight of commercial by available powdery activated carbon, 20 parts by weight of zeolite and 60 parts by weight of bentonite and then drying; grain sizes: 1.5-2.5 mm) was impregnated with 15 wt.% of the undiluted aqueous solution of iron L-ascorbate, which was prepared in Example 5.

After the impregnation, the granular activated carbon was dried at room temperature for 24 hours to prepare a granular deodorant.

On the other hand, 20 g of fowl droppings was taken in a scrubbing bottle (100 ml in volume), followed by an addition of 100 ml of purified water. After allowing the scrubbing bottle to stand for 24 hours in an incubator of 37° C., gases produced in the scrubbing bottle were purged out by 100 ml of pure air to collect them in a bag. Thereafter, 20 g of the above granular doedorant was packed in a glass tube, into which 20 liters of the gas was caused to flow as an offensive odor source from the bag at a flow rate of 2-3 liters/min. The thus-treated gas was then collected in a bag to measure offensive odor components in the bag.

Results are given in Table 3.

From the results of Table 3, it is apparent that the liquid or granular deodorant of this invention shows extremely good deodorizing effects against each of hydrogen sulfide, methyl mercaptan and ammonia.

TABLE 3

| | Offensive odor component | Concentration of offensive odor component (ppm) | | Rate of deodorization (%) |
|---|---|---|---|---|
| | | Untreated | After treatment | |
| Example 1 | Hydrogen sulfide | 38.2 | 0.04 | 99.9 |
| | Methyl mercaptan | 36.1 | 0.02 | 99.9 |
| | Ammonia | 273 | 0.33 | 99.9 |
| Example 2 | Hydrogen sulfide | 25.7 | 0.01> | >99.9 |
| | Methyl mercaptan | 7.91 | 0.01> | 99.9 |

TABLE 3-continued

| Offensive odor component | Concentration of offensive odor component (ppm) | | Rate of deodoriza- tion (%) |
| --- | --- | --- | --- |
| | Untreat- ed | After treat- ment | |
| Ammonia | 250 | 0.01 | >99.9 |

Note:
Measuring of the offensive odor components were carried out in the following manner:
[1]Hydrogen sulfide and methyl mercaptan: Quantitatively analyzed by gas chromatography.
[2]Ammonia: Subsequent to its collection in a liquid ammonia absorbent (1/50-N $H_2SO_4$ solution), the amount of ammonia in the liquid ammonia absorbent was quantitatively analyzed by absorptiometry.

EXAMPLE 7

The undiluted aqueous solution of iron L-ascorbate, which had been prepared three months ago in Example 5, was diluted with tap water to a twice volume of the undiluted aqueous solution. The resultant solution was sprayed to filter papers of 15 cm across ("Toyo Roshi-No. 5C") to give predetermined spray weights to the respective filter papers. The thus-sprayed filter papers were then dried to prepare paper-like deodorants bearing iron ascorbate respectively in adhered and dried weights of (a) 0.38 g, (b) 0.39 g, (c) 0.37 g and (d) 0.48 g.

On the other hand, a 25% aqueous ammonia solution was diluted 4 times to prepare an aqueous ammonia solution. After impregnating different filter papers each with 1 ml of the latter ammonia solution, the thus-impregnated filter papers were placed respectively in 5 plastic containers each having an internal volume of 500 ml. Thereafter, the paper-like deodorants which were the filter papers (a)-(d) were placed either in suitable combinations or singly as a one half portion or one quarter portion respectively in four of the plastic containers. Then, all the five plastic containers were hermetically sealed and then allowed to stand for predetermined time periods. Upon an elapse of each predetermined time periods, changes in offensive odor were investigated.

Investigation results are shown in Table 4.

From the results given in Table 4, it is appreciated that the paper-like deodorants according to the present invention exhibit excellent deodorizing activities against the offensive odor of ammonia.

TABLE 4

| Run No. | Deodorant (filter paper) | Ammonia smell | | |
| --- | --- | --- | --- | --- |
| | | 1 hour later | 3 hours later | 24 hours later |
| 1 | (a) + (b) | No offensive odor | No offensive odor | No offensive odor |
| 2 | (c) | Extremely small offensive odor | No offensive odor | No offensive odor |
| 3 | ½ (d) (one half portion) | No offensive odor | No offensive odor | No offensive odor |
| 4 | ¼ (d) (one quarter portion) | Strong offensive odor | Strong offensive odor | Strong offensive odor (but somewhat milder than before) |
| 5 | Not inserted | Strong offensive odor | Strong offensive odor | Strong offensive odor |

EXAMPLE 8

(A) Preparation of freshness-preserving agent:

Using water, 27.5 g of ferrous sulfate heptahydrate (molecular weight: 2778.03) was dissolved to 100 ml, followed by an addition and dissolution of 0.5 g of L-ascorbic acid to prepare an undiluted aqueous solution of iron L-ascorbate.

Then, this undiluted aqueous solution was diluted 50 times with water to prepare a freshness-preserving agent.

(B) Freshness preserving tests:

Five milliliter portions of the above freshness-preserving agent were sprayed respectively to spinach (100 g), banana (one piece, 115 g) and pork (100 g) each of which was newly bought from the market. They were then stored hermetically in respective polyethylene-made transparent bags (30 cm×25 cm) at room temperature (20° C.). Changes in the freshness of the foods and occurrence of rotting (slime, putrid smell) were observed with the lapse of time. Another test was conducted in parallel, without the treatments.

From results given in the following table, it is possible to envisaged such advantageous effects over the comparative example that use of the freshness-preserving agent allows spinach to keep its freshness for 4-5 more days, and banana to restore its original green skin from its once-yellowed skin and its texture to remain firm for 5-6 more days compared with the comparative example. Turning to the pork, it lasted for 3-4 more days compared with the comparative example.

By the way, an aqueous solution of L-ascorbic acid (10 wt.%) was also sprayed to spinach, banana and pork in the same manner as in the above tests. Test results were substantially the same as those given below for comparative example in the following table. Thus, no freshness-preserving effect was observed.

TABLE 5

| Foods | | 1st day | 2nd day | 3rd day | 4th day | 5th day |
| --- | --- | --- | --- | --- | --- | --- |
| Spinach | This invention | No change | No change | No change | No change | No change |
| | Comparative example | No change | No change | Green color of leaves reduced | Leaves somewhat shrunk | Leave color changed little by little from green to brown |
| Banana | This invention | No change | No change | Skin surface rendered blackish | Skin surface changed gradually from yellow to green | the change of skin surface from yellow to green accelerated |
| | Comparative | No change | No change | Brown spots developed on | Brown spots spread on skin | Stem was also turned to brown |

TABLE 5-continued

| | | | | skin surface | surface | |
|---|---|---|---|---|---|---|
| Pork | This invention | No change | No change | Slime occurred on the surfaces | Surface slime aggravated | Slime on the surfaces, some putrid smell occurred |
| | Comparative example | No change | Slime occurred on the surfaces, fatty parts turned to yellow some putrid smell occurred | Surface slime, yellow color of fatty parts and putrid smell, all aggravated | Surface slime, yellow color of fatty parts and putrid smell, all aggravated further | Surface slime, yellow color of fatty parts and putrid smell, all aggravated still further |

| Foods | | 6th day | 7th day | 8th day | 9th day | 10th day |
|---|---|---|---|---|---|---|
| Spinach | This invention | No change | No Change | Some black spots appeared on leaves | Black spots occurred in parts of leaves | Leaf shapes not changed but black spots spread |
| | Comparative example | Leaf surfaces dried and leaf shapes changed | Leaves turned to brownish, and leaf shapes changed further | Browning and shape changes of leaves aggravated | Browning and shape changes of leaves, further aggravated | Browning and shape changes of leaves, aggravated still further |
| Banana | This invention | Green color rendered darker on skin surface | Black spots occurred locally on skin surface | Green color of stem darkened | Green color darkened all over the banana and the texture remained firm | When the skin was peeled off, the inside was white and tasty, |
| | Comparative example | Both skin and stem became less yellow and more brown | Brown color dominated on both skin and stem, & black color appeared | Skin surface became more brown and black | Skin surface became still more brown and black, and the texture was soft | The inside was slightly yellowish with some localized brown slime, but tasty |
| Pork | This invention | Surface slime and putrid smell occurred. Fatty parts turned yellow | Visual observation impossible | — | — | — |
| Pork | Comparative example | Surface slime, yellow color of fatty parts and putrid smell, all aggravated further | Visual observation impossible | — | — | — |

EXAMPLE 9

(A) Preparation of antiseptic preservative material impregnated with iron L-ascorbate:

After dissolving 27.5 g of ferrous sulfate heptahydrate (molecular weight: 278.03) to 100 ml with water, 0.5 g of L-ascorbic acid was added and dissolved to prepare an undiluted aqueous solution of iron L-ascorbate.

Granular activated carbon (produced by a method known per se in the art, namely, extrusion-forming a mixture which contained 20 parts by weight of commercial available powdery activated carbon, 20 parts by weight of zeolite and 60 parts by weight of bentonite and then drying; grain sizes: 1.5–2.5 mm) was impregnated with 15 wt.% of the above-prepared undiluted aqueous solution of iron L-ascorbate. After the impregnation, the granular activated carbon was dried at room temperature for 24 hours to prepare a granular deodorant.

(B) Freshness preservation tests:

Spinach (100 g), banana (one piece, 110 g) and pork (100 g), each of which was newly bought from the market, were packed respectively in three polyethylene-made transparent bags (about 30 cm×25 cm). After inserting five milliliter portions of the granular freshness-maintaining agent, prepared above in (A), were placed respectively in the bags. Thereafter, the openings of the bags were hermetically sealed. They were then stored at room temperature (about 20° C.). Changes in the freshness of the foods and occurrence of rotting (slime, putrid smell) were tested along the passage of time. Another test, which was exactly the same as the above test except for the exclusion of the granular freshness-preserving agent, was conducted for the sake of comparison. Test results are shown in the following table.

From the results given in the following table, it is apparent that the freshness-preserving agent of this invention can exhibit excellent freshness-preserving activities for each of spinach, banana and pork.

TABLE 6

| Foods | | 1st day | 2nd day | 3rd day | 4th day | 5th day |
|---|---|---|---|---|---|---|
| Spinach | This invention | No change | No change | No change | No change | No change |
| | Comparative example | No change | No change | Green color of leaves reduced | Leaves shrunk slightly | Green color of leaves turned little by little to brown |
| Banana | This invention | No change | No change | No change | No change | Slightly brown spots occurred |
| | Comparative example | No change | No change | Brown spots occurred on skin surface | The brown spots spread on skin surface | Stem changed to brown too |

TABLE 6-continued

| Foods | | | | | | |
|---|---|---|---|---|---|---|
| Pork | This invention | No change | No change | Slime occurred on surfaces and fatty parts turned to yellow | Surfaces slime and yellow color of fatty parts gradually aggravated, some putrid smell | Surface slime, yellow color of fatty parts and putrid smell, all aggravated |
| | Comparative example | No change | Slime developed on surfaces and fatty parts turned to yellow, some putrid smell | Surface slime, yellow color of fatty parts and putrid smell, all aggravated | Surface slime, yellow color of fatty parts and putrid smell, all aggravated further | Surface slime, yellow color of fatty parts and putrid smell, all aggravated further |
| Foods | | 6th day | 7th day | 8th day | 9th day | 10th day |
| Spinach | This invention | Green color of leaves reduced | Green color of leaves reduced | Green color of leaves reduced and partly turned to brown | Leaves shrunk and partly turned to brown | Shrinkage and brown parts of leaves spread a little, leaf shapes changed |
| | Comparative example | Leaf surfaces dried and leaf shapes changed | The browning and shape changes of leaves, aggravated | The browning and shape changes of leaves, aggravated further | The browning and shape changes of leaves, aggravated still further | The browning and shape changes of leaves, intensified |
| Banana | This invention | Slightly brown spots occurred | Brown spots spread gradually | Brown spots spread gradually | Brown spots spread but the majority of skin surface remained still yellow | The inside was light-yellowish and free of slime |
| | Comparative example | Both skin and stem became less yellow and more brown | Both skin and stem turned more to brown and black color appeared | Brown and black spots expanded on the skin surface, | Brown and black spots expanded on the skin surface, and the inside became soft | The inside turned to light-yellowish localized brown slime, but tasty |
| Pork | This invention | Surface slime, yellow color of fatty parts and putrid smell, all aggravated | Visual ovservation impossible | — | — | — |
| | Comparative example | Surface slime, yellow color of fatty parts and putrid smell, still aggravated | Visual observation impossible | — | — | — |

EXAMPLE 10

(A) Production of ice blocks:

Using water, 27.5 g of ferrous sulfate heptahydrate (molecular weight: 278.03) was dissolved to 100 ml, in which 0.5 g of L-ascorbic acid was added and dissolved to prepare an undiluted aqueous solution of iron L-ascorbate. This undiluted aqueous solution was diluted to 300 times of volume with water. Using the thus-diluted aqueous solution, ice blocks having sizes of about 1-2 cm were produced.

(B) Freshness-preserving tests on fish and shellfish:

The above ice blocks were filled to a thickness of about 10 cm in a foamed polystyrene box (50 cm long, 30 cm wide and 30 cm deep). A paper sheet was laid over the ice blocks, on which various fish and shellfish newly bought from a market were placed. Then, the box was covered by a lid and then stored for 5 days. The temperature in the box was 3° C. for lower. As a control, fish and shellfish were stored for 5 days in a foamed polystyrene box in the same manner, using ordinary ice. Fresh fish and shellfish newly bought from the market were divided to equal half portions, which were provided as samples of the same conditions for both tests respectively.

Upon an elapsed time of 5 days, the lids were removed and the freshness of the fish and shellfish in both boxes were compared and evaluated by a panel of 10 monitors on the basis of the appearance of fish meat, the firmness of meat, feeling to eat, taste and the like. Test results are summarized in the following table.

TABLE 7

| | | Evaluation on freshness after stored for 5 days | |
|---|---|---|---|
| Fish or shellfish | Ice used | Appearance (color, luster) & firmness of meat | Feeling to eat, taste, etc. |
| Tuna fillet (100 g) | Invention ice blocks | Good brightness, and springy and firm texture | No significant difference between two samples for taste |
| | Ordinary ice | No brightness and no springy nature, soft texture | |
| Fillet of young yellowtail (100 g) | Invention ice blocks | Good brightness. without discoloration, red parts remained with vivid crimson color | No fishy smell |
| | Ordinary ice | Brightness lost. Red parts turned to brown | Fishy smell |
| Shrimps (produce of Mexico, frozen) (100 g) | Invention ice blocks | No substantial change | Extremely slight fishy smell |
| | Ordinary ice | No substantial change | Strong fishy smell |
| Octopus (100 g) | Invention ice blocks | Firm texture | Good in both feeling to bite and taste |

TABLE 7-continued

| Fish or shellfish | Ice used | Appearance (color, luster) & firmness of meat | Feeling to eat, taste, etc. |
|---|---|---|---|
| Saurel (100 g) | Ordinary ice | Soft texture | Poor feeling to bite |
| | Invention ice blocks | Good brightness and color | Slight fishy smell |
| Flounder (100 g) | Ordinary ice | No brightness | Strong fishy smell |
| | Invention ice blocks | Good brightness | Good feeling to bite |
| Pen shell meat (100 g) | Ordinary ice | Slightly discolored | |
| | Invention ice blocks | No substantial change | Good feeling to bite |
| | Ordinary ice | No substantial change | Poor feeling to bite |

Totally judging from the results in the above table, it is understood that the freshness was significantly reduced in the control test, in which ordinary ice was used, although the storage conditions corresponded to the winter; and the present invention is able to avoid such freshness reduction and hence to preserve the freshness of fish and shellfish under good conditions with good liveliness and feeling to bite but without fishy smell.

We claim:

1. An oxidation-resistant chemical composition effective as a deodorizing agent, a bactericidal agent, a food preserving agent, or a pollutant coagulating agent, which comprises divalent iron ions and L-ascorbic acid, said L-ascorbic acid being present in an amount of 2 to 10 parts by weight per 100 parts by weight of the divalent iron ions, expressed in terms of metallic iron.

2. The oxidation-resistant chemical composition of claim 1 in the form of an aqueous solution wherein the divalent iron ions are present in a concentration of from 0.15 weight percent, calculated in terms of the metallic iron, up to the solubility of the divalent iron ions in the aqueous solution.

3. A solid material impregnated with the composition of claim 2.

4. The oxidation-resistant chemical composition of claim 2 wherein the chemical composition solution is a deodorant wherein the total concentration of L-ascorbic acid and divalent iron compound is present in the aqueous solution in a concentration of 0.1 to 30 weight percent.

5. The oxidation-resistant chemical composition of claim 3 wherein the solid material is selected from the group consisting of paper, synthetic paper, a fabric, a non-woven fabric, and a porous material.

6. The oxidation-resistant chemical composition of claim 5 wherein the porous material is selected from the group consisting of activated carbon, zeolite, bentonite, kaolin, pearlite sepiolite, diatomaceous earth, silica and alumina.

7. The oxidation-resistant chemical composition of claim 3 wherein the total amount of L-ascorbic acid and divalent iron ions to be carried by the solid material is 0.5 to 20 parts by weight per 100 parts by weight of the solid material.

8. The oxidation-resistant chemical composition of claim 1, wherein the divalent irons and ascorbic acid form a complex.

9. An aqueous coagulant solution for water pollutants comprising L-ascorbic acid and an iron (II) compound in a total concentration of 0.01 to 20 weight percent based on the weight of the coagulant solution.

* * * * *

UNITED STATES PATENT AND TRADEMARK OFFICE
CERTIFICATE OF CORRECTION

PATENT NO. : 4,745,129
DATED : May 17, 1988
INVENTOR(S) : Ikari et al

It is certified that error appears in the above-identified patent and that said Letters Patent is hereby corrected as shown below: On the title page In the category "[73] Assignee:" change "Technology and Minato Sangyo Co. Ltd., Tokyo, Japan" to --Director-General of Agency of Industrial Science and Technology and Minato Sangyo Co., Ltd., Tokyo, Japan--.

Signed and Sealed this

Twenty-third Day of May, 1989

Attest:

DONALD J. QUIGG

*Attesting Officer*  *Commissioner of Patents and Trademarks*